US011167816B2

(12) United States Patent
Bailey

(10) Patent No.: US 11,167,816 B2
(45) Date of Patent: Nov. 9, 2021

(54) CONTROL OF A TWO-WHEELED SELF-BALANCING VEHICLE

(71) Applicants: Lit Motors Corporation, San Francisco, CA (US); David Arthur Bailey, Glendale, AZ (US)

(72) Inventor: David Arthur Bailey, Glendale, AZ (US)

(73) Assignee: Lit Motors Corporation, San Francisco, CA (US)

( * ) Notice: Subject to any disclaimer, the term of this patent is extended or adjusted under 35 U.S.C. 154(b) by 76 days.

(21) Appl. No.: 16/085,975

(22) PCT Filed: Mar. 17, 2017

(86) PCT No.: PCT/US2017/023025
§ 371 (c)(1),
(2) Date: Sep. 17, 2018

(87) PCT Pub. No.: WO2017/161308
PCT Pub. Date: Sep. 21, 2017

(65) Prior Publication Data
US 2019/0077480 A1    Mar. 14, 2019

Related U.S. Application Data

(60) Provisional application No. 62/309,892, filed on Mar. 17, 2016.

(51) Int. Cl.
*B62K 11/00* (2006.01)
*G01C 19/04* (2006.01)
(Continued)

(52) U.S. Cl.
CPC ......... *B62K 11/007* (2016.11); *A61M 1/0037* (2013.01); *A61M 1/0058* (2013.01);
(Continued)

(58) Field of Classification Search
CPC ............... B62K 11/007; A61M 1/0058; A61M 1/0037; A61M 1/0062; A61M 1/0088;
(Continued)

(56) References Cited

U.S. PATENT DOCUMENTS 4,200,168 A    4/1980 Moog
8,919,788 B2   12/2014 Kim et al.
(Continued)

FOREIGN PATENT DOCUMENTS

WO    2013130656 A1    9/2013
WO    2013130659 A1    9/2013

OTHER PUBLICATIONS

Colvin, Gregory R., "Development and Validation of Control Moment Gyroscopic Stablization," Ohio State University, Feb. 2014, 29 pages.
Extended European Search Report for European Patent Application No. 17767657.4, dated Jan. 30, 2020, 9 pages.
(Continued)

*Primary Examiner* — Brian P Sweeney
(74) *Attorney, Agent, or Firm* — Elliott, Ostrander & Preston, P.C.

(57) ABSTRACT

A control system for a two-wheeled vehicle, including an inertial measurement unit (IMU); one or more control moment gyroscopes (CMGs); one or more CMG controllers to control the one or more CMGs; an accelerometer to measure a y-axis acceleration for the vehicle, the y-axis being perpendicular to a direction of travel of the vehicle and parallel to a ground surface; and a processing element to calculate a roll angle for the vehicle based at least in part on the y-axis acceleration measured by the accelerometer, determine a force component based at least in part on the
(Continued)

calculated roll angle, and generate a CMG command for a CMG gimbal rate based at least in part on the determined force component.

19 Claims, 7 Drawing Sheets

(51) Int. Cl.
  *A61M 1/00* (2006.01)
  *B62J 45/40* (2020.01)
  *B60W 10/20* (2006.01)
  *G05D 1/08* (2006.01)

(52) U.S. Cl.
  CPC ........ *A61M 1/0062* (2013.01); *A61M 1/0088* (2013.01); *G01C 19/04* (2013.01); *A61M 2205/16* (2013.01); *A61M 2205/17* (2013.01); *B60W 10/20* (2013.01); *B62J 45/40* (2020.02); *G05D 1/0891* (2013.01)

(58) Field of Classification Search
  CPC .......... A61M 2205/16; A61M 2205/17; G01C 19/04; B62J 45/40; B60W 10/20; G05D 1/0891
  USPC ........................................................ 701/124
  See application file for complete search history.

(56) References Cited

U.S. PATENT DOCUMENTS

| | | |
|---|---|---|
| 2011/0295449 A1 | 12/2011 | Kreider et al. |
| 2013/0233100 A1 | 9/2013 | Kim |
| 2013/0238233 A1 | 9/2013 | Kim et al. |
| 2014/0054867 A1* | 2/2014 | Kim ...................... B60G 21/08 |
| | | 280/5.509 |

OTHER PUBLICATIONS

International Preliminary Report on Patentability for International Patent Application No. PCT/US2017/023025, dated Sep. 18, 2018, 6 pages.
International Search Report and Written Opinion for International Patent Application No. PCT/US2017/023025, dated May 29, 2017, 7 pages.
Lam, Pom Yuan, "Gyroscopic Stabilization of a Kid-Sized Bicycle," 2011 IEEE 5th International Conference on Cybernetics and Intelligent Systems, Sep. 17-19, 2011, pp. 247-252.
Yetkin, Harun, et al. "Gyroscopic Stabilization of an Unmanned Bicycle," Conference Paper in Proceedings of the American Control Conference, Jun. 2014, 7 pages.
Office Action for Taiwan Patent Application No. 106109036, dated Apr. 20, 2020, 12 pages.
Notice of Grant for European Patent Application No. 17767657.4, dated Nov. 2, 2020, 30 pages.

* cited by examiner

CONTROL OF A TWO-WHEELED SELF-BALANCING VEHICLE

CLAIM OF PRIORITY

This application is a 3.71(c) application claiming priority to PCT Patent Application PCT/US17/23025 filed on Mar. 17, 2017, which claims priority to U.S. Provisional Application No. 62/309,893 filed on Mar. 17, 2016, the entire contents of which are hereby incorporated by reference herein.

FIELD OF THE INVENTION

Embodiments of the invention generally pertain to transportation vehicles, and more particularly to control of a two-wheeled self-balancing vehicle.

BACKGROUND

In the control of a vehicle, balancing controls for a vehicle may commonly start with broomstick balancers, or an inverted pendulum. For example, when designing the Saturn-5 launch vehicle, the control team designed and built two broom stick balancers, a one axis version and a two axis version. The method of sensing the unbalance was to measure the angle of the broomstick and control the angle to be 90 degrees to the base.

The control method involved moving the base to be directly under the center of gravity of the broomstick. In the rocket, four of the rocket motors were gimbaled to allow a side thrust and move the base of the rocket directly behind the center of gravity of the rocket. The launch vehicle uses an Inertial Measurement Unit (IMU) to determine the attitude and that is used in the control to control the direction of the rocket.

However, the control of a two-wheeled vehicle involves forces that are more complex than such rocket guidance calculations, and thus the application of conventional control concepts are not sufficient to address the control operation.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. It should be appreciated that the following figures may not be drawn to scale.

Descriptions of certain details and implementations follow, including a description of the figures, which may depict some or all of the embodiments described below, as well as a discussion of other potential embodiments or implementations of the inventive concepts presented herein. An overview of embodiments of the invention is provided below, followed by a more detailed description with reference to the drawings.

DESCRIPTION

Embodiments of the invention describe methods, apparatuses, and systems for control of a two-wheeled self-balancing vehicle. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Figure 1:
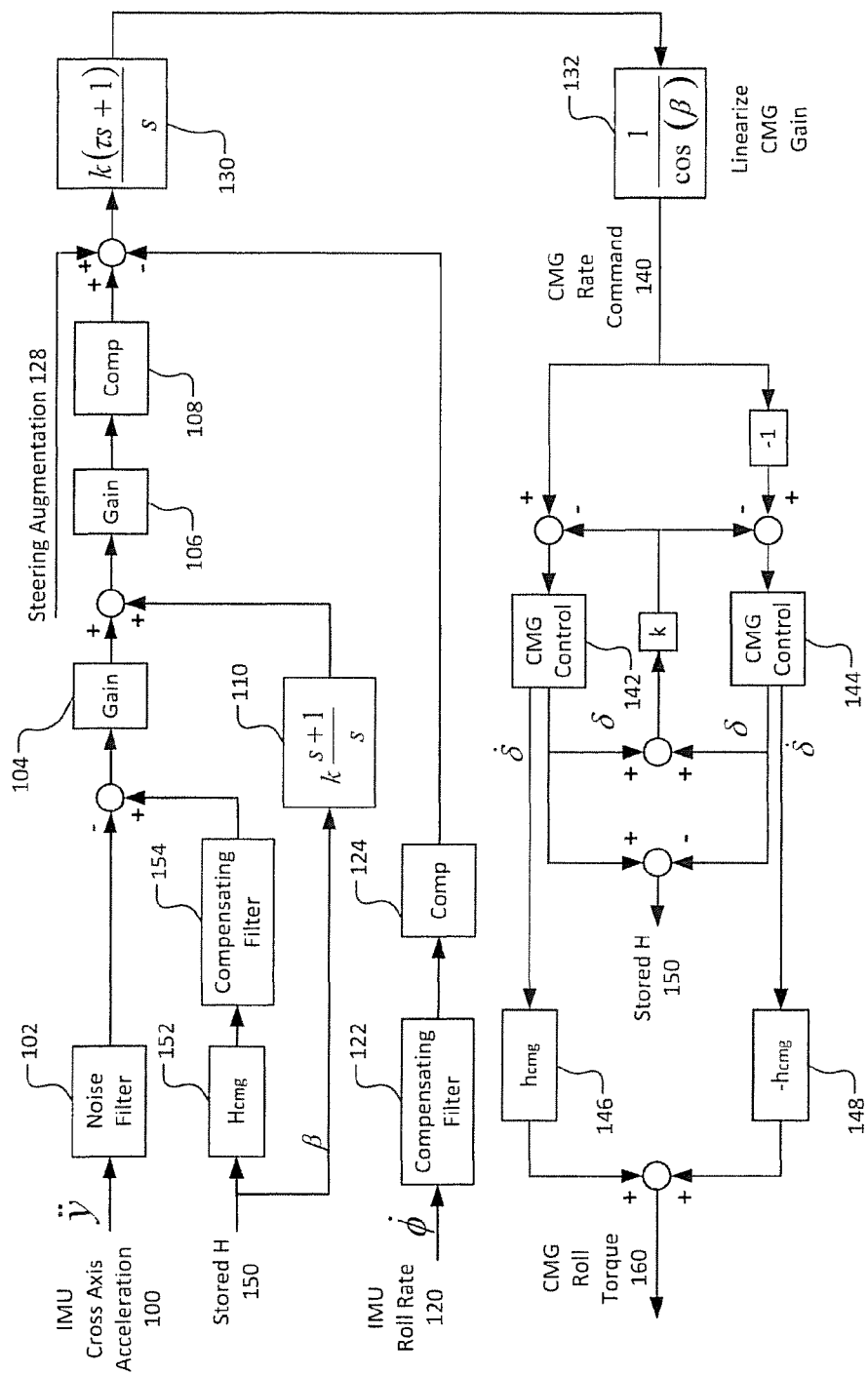
FIG. 1 is a control block diagram for a two-wheeled self-balancing vehicle according to an embodiment.

FIG. 1 is a control block diagram for a two-wheeled self-balancing vehicle according to an embodiment. In some embodiments, the control flow provides for IMU cross axis acceleration 100 for the vehicle being provided to a noise filter 102. A control value $H_{cmg}$ 152 is also applied to stored control value H 150, and then is filtered by a compensating filter 154 (which may be the same order as the noise filter 102). The output of the noise filter 102 is subtracted from the output of the compensating filter 154, with the difference being subjected to a first gain 104, which is then added to the stored H value 150 times the value k×(s+1)/s (element 110, wherein k is a constant and s is the Laplace operator). The resulting value is multiplied by a second gain 106 and then compensation 108 is added.

In some embodiments, an IMU roll rate 120 is filtered by a second compensating filter 122 (wherein the compensating filter may be one order less than the noise filter) to which is added compensation 124. The result is subtracted from compensation 108 to generate a difference. In some embodiments, a steering augmentation 128 is added to the difference, wherein the steering augmentation is further described below.

In some embodiments, the result is multiplied times the value k×(τs+1)/s (element 130, where τ is the time constant of the lead term in the transfer function). CMG gain is then linearized by 1/cos(β) (element 132) to generate the CMG rate command 140, the command being provided to the first CMG control 142 and second CMG control 144, producing CMG gimbal angles δ. The sum of the gimbal angles is fed back in the generation of the CMG rate command, and the difference between the CMG gimbal angles produces the stored control value H 150. As shown, the sum of δ dot values from the CMG controls 142-144 times $h_{cmg}$ 146 and $-h_{cmg}$ 148 values is the CMG roll torque 160.

Gyroscopes are angular momentum storage elements built around a rotating flywheel. The flywheel acts as a torque actuator. Rotating the angular momentum vector produces a torque in the direction of rotation and perpendicular to the angular momentum vector. The reaction torque to this generated torque is applied to the vehicle. Using a pair of CMGs with one angular momentum vector pointing up and the other angular momentum pointing down and rotating them in opposite directions results in torque in a single axis. The axis of interest is the roll axis. The angular momentum vectors aren't required to be up and down, but rather arranged such the nominal vector sum is zero, and with sufficient accuracy such that the sum of the angular momentum vectors can made to grow and remain directed along the roll axis of the vehicle. Symmetry results in the equal and opposite angular moment being relayed in the vehicle. A change in length of the angular momentum vector results in torque being applied to the vehicle. A "CMG" generally describes a gyroscope specifically applied for attitude control of rigid bodies (traditionally used in satellites and spacecraft). As described below, with various configurations, a CMG system is applied in a two-wheeled self-balancing vehicle.

The control of a two-wheeled self-balancing vehicle, also referred to as a bike herein, involves forces that are more complex than a rocket example. A sensor is required to point the Center of Gravity (CG) to the point of contact on the ground. When a bike is traversing a corner there is a large centrifugal force that has to be counteracted by the gravitational force. If the coordinate system origin is at the contact of the back tire with the ground, then the x axis is the direction from the back tire to the front tire. The y axis then is perpendicular to the direction of travel and parallel to the ground and pointing to the right of the direction of travel, and the z axis is into the ground.

In some embodiments, an accelerometer is utilized to measure an angle in a two-wheeled vehicle control system. In such an implementation, an accelerometer detecting acceleration in the y-direction in body coordinates (coordinates fixed in relation to the two-wheeled vehicle) may be a more useful sensor than a gyroscope measuring attitude based on world coordinates (coordinates in relation to the earth). There are five basic components to the y-axis acceleration if the Inertial Measurement Unit (IMU) is mounted significantly above the ground, which is the roll axis. The three large components are the acceleration due to centrifugal force, the acceleration due to the gravitational force, and the acceleration due to the CMGs. The two minor accelerations at nominal speeds are due to the change in direction of the angular momentum of the front and back wheels.

Balance control can't use y-axis acceleration by itself, but rather the sum of all the accelerations except the CMG acceleration is the quantity needed to control the balance. To convert y-axis acceleration to the angle of the net force vector certain calculations are needed. The linear acceleration is converted to roll acceleration by dividing by the distance from the roll axis (ground) to the accelerometer, if the IMU is centered in the vehicle. If the vehicle is not in a skid then forces from the gravity, centrifugal force are countered by forces between the pavement and the tires. The forces of the tire pavement interface do not cause a torque, because they act through the roll axis. With the roll acceleration, the roll torque can be determined by dividing by the roll axis moment of inertia. The net torque after the torque generated by the CMGs is removed is the disturbance torque. The net torque is the force multiplied by the distance from the CG to the pavement times the sine of the desired roll angle. For small angles sine of the angle is approximately the angle. This angle is the variation from vertical if the bike is stopped or driving straight. It is also the angle that is the error between going around a perfectly coordinated curve and starting to roll the bike.

The roll angle for the attitude from an IMU can be calculated from the direction of the front tire, and the forward velocity of the bike, if the tires do not slip.

In some embodiments, the improved measurement utilizing the accelerator unit enables the control to instantly detect that a tire is slipping because the lateral acceleration changes, and thus the control can react to the slippage. This can prevent a fall when traveling around a curve.

As expressed in an equation:

$$\ddot{\varphi} = \{(m_{tf} \cdot R_{tfc} + m_f \cdot h_f + m_{tr} \cdot R_{trc})g \cdot \sin(\varphi) + (\dot{\delta}_1 \cos(\delta_1) - \dot{\delta}_2 \cos(\delta_2))H_{CMG} + Q_{rtc} + Q_{trx} + Q_{tfx}\}/J_{xxeff} \quad [1]$$

Where:
ø is roll angle
$m_{tf}$ is mass tire front
$R_{tfc}$ is radius of tire front contact
$m_f$ is mass of frame
$h_{cg}$ if height of the frame center of gravity
$m_{tr}$ is the mass of tire rear
$R_{trc}$ is the radius of tire rear at contact
g gravitational constant
δ CMG gimbal angle
$H_{CMG}$ is the angular momentum of the CMG
$Q_{rtc}$ is the torque from the centrifugal roll torque
$Q_{trx}$ is the rear tire toque about x axis due to angular momentum change
$Q_{tfx}$ is the front tire torque about the x axis due to angular momentum change
$J_{xxeff}$ is the effective moment of inertia about the x axis
The centrifugal force terms all have a common term.

$$\omega^2 \cdot R_{turn} = \text{Speed}^2 \cdot \tan(\psi)/p \quad [2]$$

Psi (ψ) is the angle of the front tire and p is the wheel base. The three centrifugal forces are this term times the mass of each tire and the mass of the frame. The torques produced are the height of the center of gravity of each component times the cos of the roll angle. If the steering angle is constant then the centrifugal torque increases as the square of the speed and decreases by the fact that the roll angle increases and the torsion arm get smaller. The angular momentum torque from the wheels is the angular momentum vector of each wheel. This is a function of roll angle for the rear wheel, and the steering angle and roll angle for the front wheel. The cross product of the turning angular rate vector with the angular momentum vector results in a torque vector and the component of this vector with the roll axis is the roll torque due to change in direction on the wheel angular momentum.

The accelerometer term is the roll axis angle acceleration times the lever arm from the contact point on the road to the IMU. The y-axis imbedded in the bike rolls with the bike. Taking the y-axis acceleration dividing by the IMU height and multiplying by the bike CG height scales the acceleration to the center of gravity. Next, the component of the acceleration due to the CMG torque is removed, and this is multiplied by the effective moment of inertia about the roll axis, which results in a force component. This result is the total force acting on the bike CG times the sine of the angle between the direction of the force and the direction to the roll axis. This is the parameter needed for control, and such parameter immediately detects wheel slip and accurately calculates the geometry of the bike dynamics. This term is faster and more accurate than using the IMU attitude and trying to correct the IMU attitude for bike dynamics.

Figure 2:
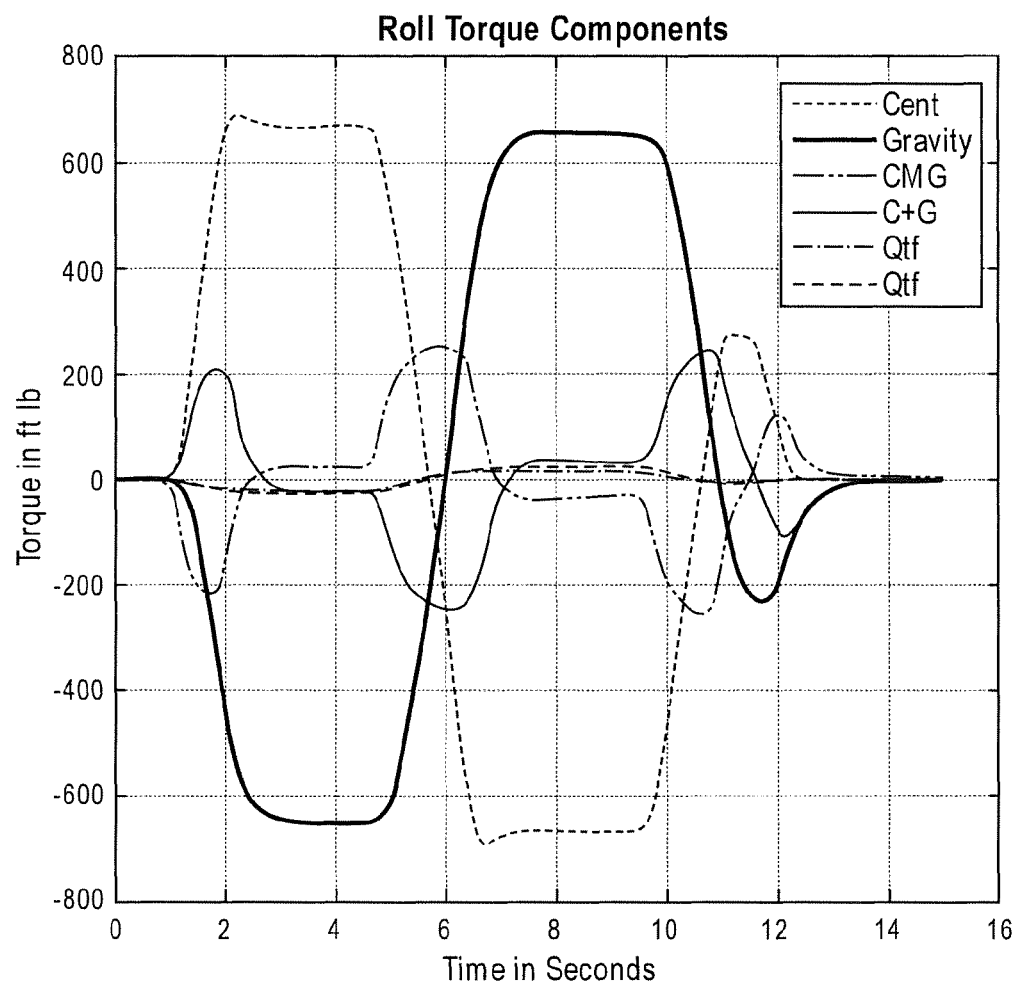
FIG. 2 is an illustration of roll torque components for a two-wheeled vehicle at a speed of 25 miles per hour (MPH)

FIG. 2 is an illustration of roll torque components for a two-wheeled vehicle at a speed of 25 miles per hour (MPH). Steering feedforward is a new term that arises from studying the bike roll torque components. At 25 MPH, in performing an aggressive dog leg turn combination the roll torque components are as illustrated in FIG. 2.

In this illustration, the centrifugal force torque overshoots because the bike gets fully into the turn before the CMGs can get the bike rolled over to compensate for the centrifugal force. The gravity torque ideally will match the centrifugal torque and the sum of all the torques less the CMG torque will become zero. In this case the CMGs have to produce well over 200 foot pounds of torque to control the bike.

To identify the term that leads the centrifugal force, the front wheel angle is differentiated and plotted against the CMG gimbal rate command.

Figure 3:
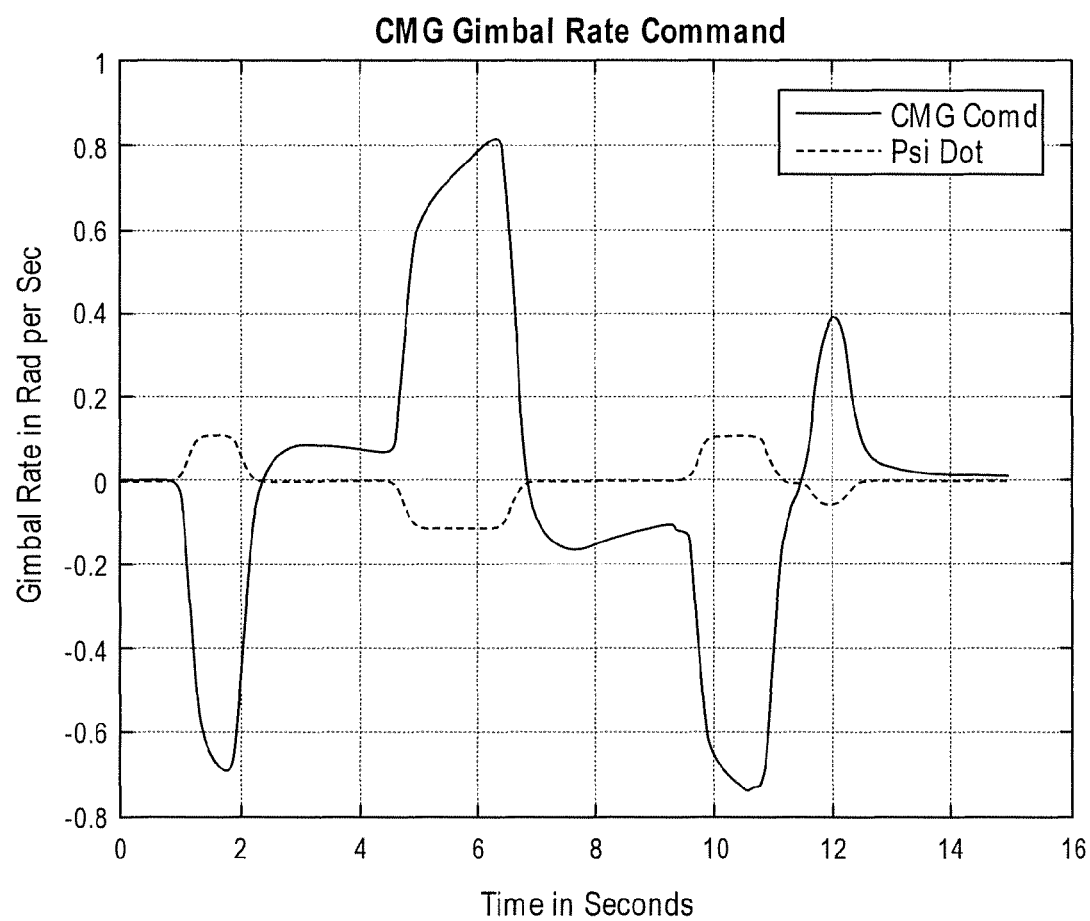
FIG. 3 is an illustration of front wheel rate and CMG gimbal rate in the operation of a two-wheeled vehicle.

FIG. 3 is an illustration of front wheel rate and CMG gimbal rate in the operation of a two-wheeled vehicle. Psi, the front wheel angle, generates the centrifugal force. With the correct scale factor the steering derivative could push the CMG gimbal rate command and cause the bike to roll over faster. Further, if the bike rolled over faster, the gravitational torque would better compensate for the centrifugal torque.

Figure 4:
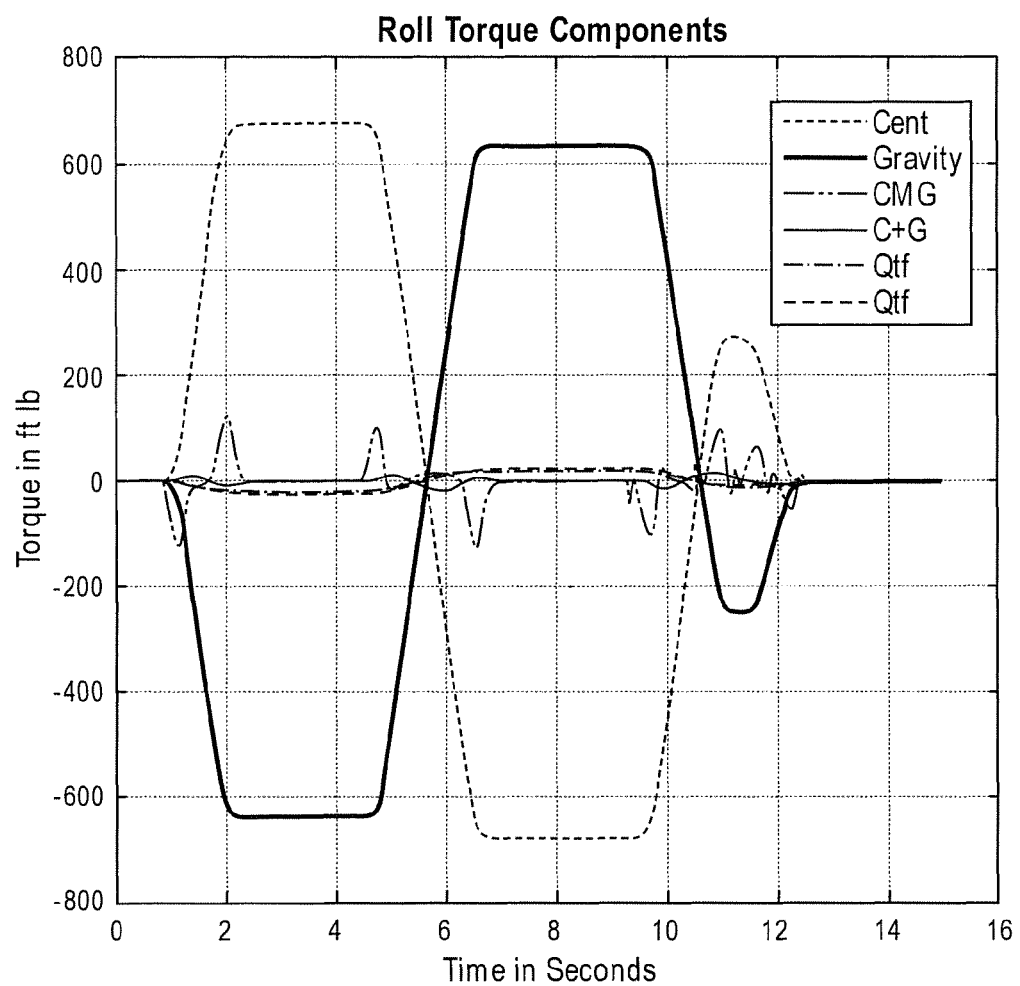
FIG. 4 is an illustration of CMG gimbal rate and the derivative of steering for a two-wheeled vehicle according to an embodiment.

FIG. 4 is an illustration of CMG gimbal rate and the derivative of steering for a two-wheeled vehicle according to an embodiment. In FIG. 4, the psi dot term is the same as illustrated in FIG. 3, but the CMG rate command is quicker, while the amplitude is smaller. The steering compensation causes the centrifugal force torque and gravitational torque to more closely match, resulting in a lower CMG torque requirement. In some embodiments, the steering rate measurement may be utilized for improved control of a two-wheeled, self-balancing vehicle.

Figure 5:
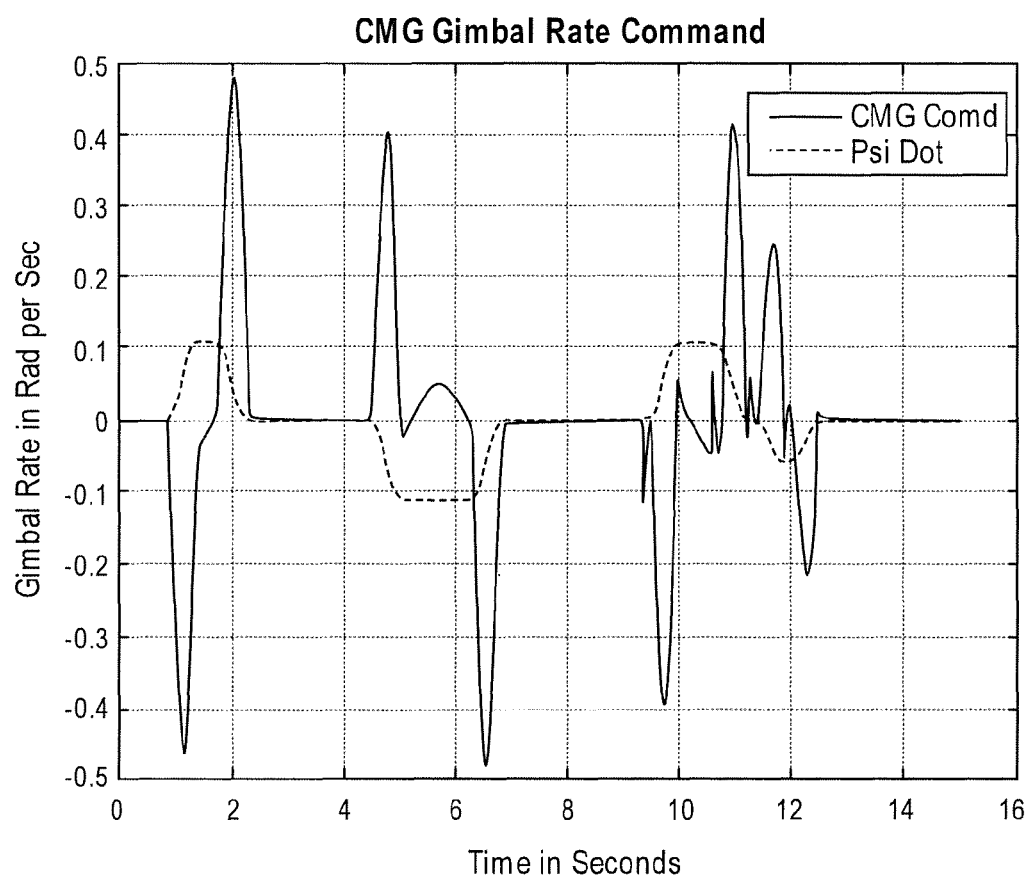
FIG. 5 is an illustration of CMG gimbal rate with steering compensation for control of a two-wheeled vehicle according to an embodiment.

FIG. 5 is an illustration of CMG gimbal rate with steering compensation (psi dot, or $\dot{\varphi}$) for control of a two-wheeled vehicle according to an embodiment. In FIG. 5, the CMG gimbal rate reflects the CMG torque and the steering rate ($\dot{\varphi}$) lead helps to push the bike over more quickly, resulting in a much smaller CMG compensation required. The centrifugal torque and the gravitational torques almost mirror each other. The torques from rotating the angular momentum of the front and rear wheels remain small.

Figure 6A:
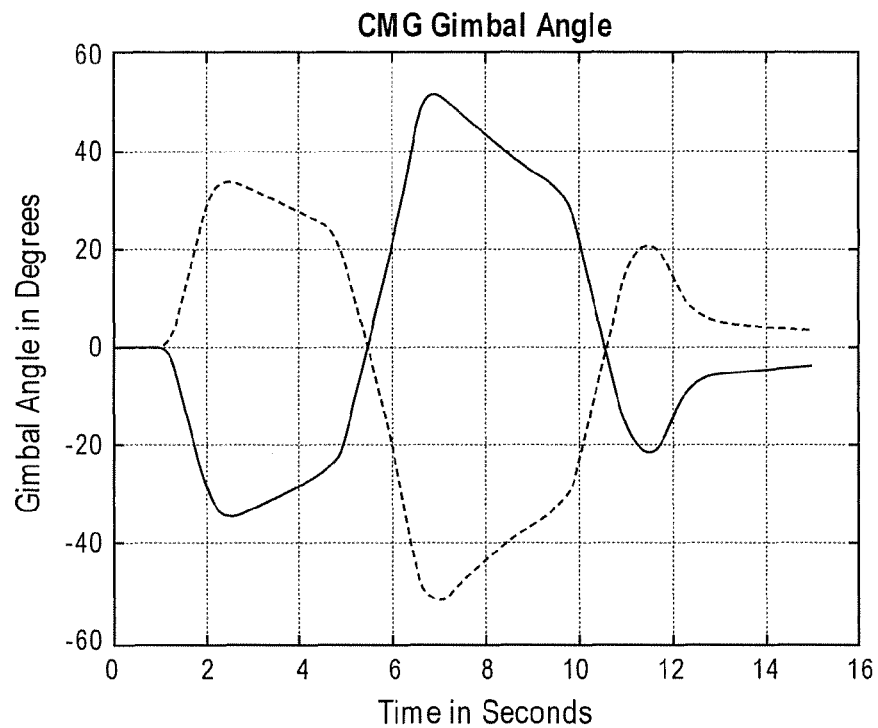
FIGS. 6A and 6B are illustrations of CMG gimbal angle excursions before and after compensation according to an embodiment.
Figure 6B:
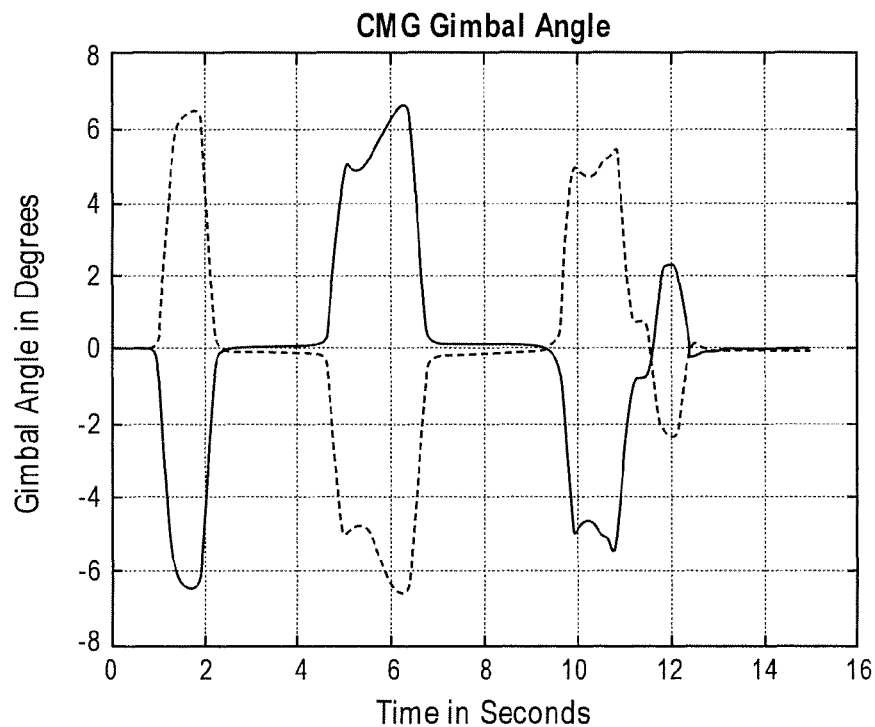

FIGS. 6A and 6B are illustrations of CMG gimbal angle excursions before and after compensation according to an embodiment. In FIG. 6B after compensation, the compensation has reduced the CMG gimbal angle excursion significantly in comparison with the requirements for before compensation illustration in FIG. 6A. This is important because the CMGs generally only have a useful range of about plus or minus 70 degrees.

Compensating for the centrifugal force induced torque has a speed term that has to be considered.

The equation for centrifugal force is:

$$F_c = M \cdot v^2 \cdot r \qquad [3]$$

The force is proportional to the velocity squared and with a fixed geometry curve the force application is proportional to the velocity term. This means the difficulty in making a curve increases as velocity cubed. In the case of the motorcycle the radius of the curve is a function of the steering angle (psi).

$$\tan(\psi) = \frac{p}{r} \qquad [4]$$

$$r = \frac{p}{\tan(\psi)} \qquad [5]$$

$$F_c = \frac{m \cdot v^2}{p} \frac{\sin(\psi)}{\cos(\varphi)} \qquad [6]$$

To anticipate a force, the time derivative of the force may be applied:

$$\dot{F}_c = \frac{m}{p} 2 \cdot v \cdot \dot{v} \frac{\sin(\psi)}{\cos(\varphi)} + \frac{m \cdot v^2}{p} \frac{\cos(\psi)}{\cos(\varphi)} \dot{\psi} - \frac{m \cdot v^2}{p} \frac{\sin^2(\psi)}{\cos^2(\varphi)} \dot{\psi} \qquad [7]$$

If the velocity is a constant then the time derivative is zero.

$$\dot{F}_c = \frac{m \cdot v^2}{p} \left(1 - \frac{\sin^2(\psi)}{\cos^2(\varphi)}\right) \dot{\psi} \qquad [8]$$

For a fixed geometry, turn psi dot is proportional to velocity, and force is proportional to velocity cubed.

As a result, the ideal compensation may be expressed as:

$$\text{Comp} = -k \cdot \dot{\psi} \cdot v^2 \qquad [9]$$

The k in the linear region of operation is larger than the k required when the CMG gimbal rate commands saturate. Calculating the k for intermediate speed and for a speed resulting in at an extreme roll angle allows a compensation fit of the form:

$$\text{Comp} = -k \cdot \dot{\psi} \cdot v^n \qquad [10]$$

In this form k is a constant and n is rational instead of an integer.

In some embodiments, the final control topology consideration is steering augmentation. Using computer compensated steering reduces the load on the CMG as well as providing a backup control in the unlikely circumstance that both CMGs were to fail on the same trip. By taking the psi dot off of the steering wheel and adding the steering augmentation between the steering wheel and the front wheel, the steering augmentation will not reduce the feedforward into the CMG gimbal rate command. The steering augmentation is a correction to the commanded steering that starts the bike to roll in the correct direction. As such the steering augmentation is in the opposite direction as the steering command. This is accomplished by using a lead-lag compensation term with the lead in the right hand complex plane.

Figure 7:
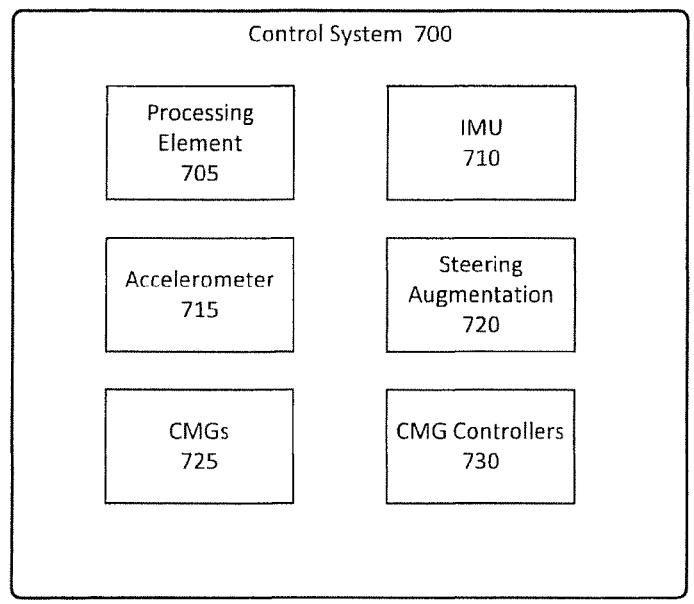
FIG. 7 is an illustration of components of a control system for a two-wheeled self-balancing vehicle.

FIG. 7 is an illustration of elements of a control system for a two-wheeled self-balancing vehicle according to an embodiment. In some embodiments, the control system 700 includes sensors and control elements for a two-wheeled self-balancing vehicle, including the following:

705: A processing element to process data for the control of the vehicle.

710: An inertial measurement unit (IMU) to measure specific force and angular rate for the vehicle.

715: An accelerometer to measure a lateral acceleration of the vehicle.

720: A steering augmentation element to augment a steering command for the vehicle.

725: One or more CMGs, which may include a first CMG and a second CMG, the first and second CMGs having angular momentum vectors pointing in opposite directions.

730: One or more CMG controllers to control a gimbal rate for the one or more CMGs.

In some embodiments:

(1) A control system for a two-wheeled vehicle is to utilize y-axis acceleration, instead of IMU angle, to measure the roll axis angle.

(2) A control system for a two-wheeled vehicle is to utilize steering rate to cause the CMG gimbal rate to move earlier.

(3) A control system for a two wheel vehicle is to measure the steering rate of the steering wheel command, instead of the front wheel turning rate, and thus separates the operator action from the wheel motion for generating rate compensation. This reduces the interference between steering augmentation and CMG gimbal rate compensation.

In some embodiments, a control system for a two-wheeled vehicle includes an inertial measurement unit (IMU); one or more control moment gyroscopes (CMGs); one or more CMG controllers to control the one or more CMGs; an accelerometer to measure a y-axis acceleration for the vehicle, the y-axis of the vehicle being perpendicular to a direction of travel of the vehicle and parallel to a ground surface; and a processing element to calculate a roll angle for the vehicle based at least in part on the y-axis acceleration measured by the accelerometer, determine a force component based at least in part on the calculated roll angle, and generate a CMG command for a CMG gimbal rate based at least in part on the determined force component.

In some embodiments, the force component is a total force on a center of gravity of the vehicle multiplied times a sine of an angle between the direction of the force and the direction to a roll axis.

In some embodiments, the measurement of y-axis acceleration by the accelerometer enables detection of slippage of a tire of the vehicle based on a change in lateral acceleration.

In some embodiments, the one or more CMGs include two CMGs with angular momentum vectors in opposite directions.

In some embodiments, the processing element determines a steering augmentation value to modify a steering command for the vehicle, the processing element to modify the determination of the force component and CMG command based on the steering augmentation value.

In some embodiments, a control system for a two-wheeled vehicle includes an inertial measurement unit (IMU); one or more control moment gyroscopes (CMGs); one or more CMG controllers to control the one or more CMGs; a steering augmentation unit to augment a steering command by a determined steering augmentation value; and a processing element to modify a determination of a CMG command for the one or more CMG controllers based at least in part on application of the steering augmentation value.

In some embodiments, application of the steering augmentation value is to cause a CMG gimbal rate to be advanced.

In some embodiments, the application of the steering augmentation value is to reduce an amount of CMG compensation required for control of the vehicle.

In some embodiments, the steering augmentation is to start the vehicle to roll in a correct direction, the steering augmentation being in an opposite direction as the steering command.

In some embodiments, the steering augmentation is to operate as a backup CMG control upon a failure of the one or more CMGs.

In some embodiments, a method includes measuring with an accelerometer a y-axis acceleration for a two-wheeled vehicle, a y-axis of the vehicle being perpendicular to a direction of travel of the vehicle and parallel to a ground surface, the vehicle including one or more control moment gyroscopes (CMGs); calculating a roll angle for the vehicle based at least in part on the y-axis acceleration measured by the accelerometer; determining a force component based at least in part on the calculated roll angle; and generating a CMG command for a CMG gimbal rate based at least in part on the determined force component.

In some embodiments, the force component is a total force on a center of gravity of the vehicle multiplied times a sine of an angle between the direction of the force and the direction to a roll axis.

In some embodiments, the method further includes detecting slippage of a tire of the vehicle based on a change in lateral acceleration using the measurement by the accelerometer.

In some embodiments, the method further includes determining a steering augmentation to modify a steering command.

In some embodiments, the generation of the CMG command is further based at least in part on the steering augmentation.

In some embodiments, application of the steering augmentation is to cause a CMG gimbal rate to be advanced.

In some embodiments, application of the steering augmentation is to reduce an amount of CMG compensation required for control of the vehicle.

In some embodiments, the method further includes providing a backup CMG control utilizing the steering augmentation upon a failure of the one or more CMGs.

In some embodiments, the steering augmentation is to start the vehicle to roll in a correct direction, the steering augmentation being in an opposite direction as the steering command.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

Some portions of the detailed description above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent series of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the discussion above, it is appreciated that throughout the description, discussions utilizing terms such as "capturing," "transmitting," "receiving," "parsing," "forming," "monitoring," "initiating," "performing," "adding," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments of the disclosure also relate to an apparatus for performing the operations herein via circuitry, logic, or processor-executed software modules. This apparatus may be specially constructed for the required purposes, or it may comprise a general purpose computer selectively activated or reconfigured by a computer program stored in the computer. Such a computer program may be stored in a non-transitory computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

Some portions of the detailed description above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "capturing", "determining", "analyzing", "driving", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The algorithms and displays presented above are not inherently related to any particular computer or other apparatus. Various general purpose systems may be used with programs in accordance with the teachings herein, or it may prove convenient to construct a more specialized apparatus to perform the required method steps. The required structure for a variety of these systems will appear from the description below. In addition, the present disclosure is not described with reference to any particular programming language. It will be appreciated that a variety of programming languages may be used to implement the teachings of the disclosure as described herein.

Reference throughout this specification to "one embodiment" or "an embodiment" means that a particular feature, structure, or characteristic described in connection with the embodiment is included in at least one embodiment of the present disclosure. Thus, the appearances of the phrases "in one embodiment" or "in an embodiment" in various places throughout the above specification are not necessarily all referring to the same embodiment. Furthermore, the particular features, structures, or characteristics may be combined in any suitable manner in one or more embodiments.

The present description, for purpose of explanation, has been described with reference to specific embodiments. However, the illustrative discussions above are not intended to be exhaustive or to limit the disclosure to the precise forms disclosed. Many modifications and variations are possible in view of the above teachings. The embodiments were chosen and described in order to best explain the principles of the disclosure and its practical applications, to thereby enable others skilled in the art to best utilize the various embodiments with various modifications as may be suited to the particular use contemplated.

Methods and processes, although shown in a particular sequence or order, unless otherwise specified, the order of the actions may be modified. Thus, the methods and processes described above should be understood only as examples, and may be performed in a different order, and some actions may be performed in parallel. Additionally, one or more actions may be omitted in various embodiments of the invention; thus, not all actions are required in every implementation. Other process flows are possible.

What is claimed is:

1. A control system for a two-wheeled vehicle comprising:
    an inertial measurement unit (IMU);
    one or more control moment gyroscopes (CMGs);
    one or more CMG controllers to control the one or more CMGs;
    an accelerometer to measure a y-axis acceleration for the vehicle, the y-axis of the vehicle being perpendicular to a direction of travel of the vehicle and parallel to a ground surface, wherein the accelerometer to measure the y-axis acceleration for the vehicle comprises the accelerometer detecting a leakage in a value of sine of an error angle times a vector sum of a gravitational acceleration and a centrifugal acceleration of the two-wheeled vehicle; and
    a processor to:
    calculate a roll angle for the vehicle based at least in part on the y-axis acceleration measured by the accelerometer,
    determine a force component based at least in part on the calculated roll angle, and
    generate a CMG command for a CMG gimbal rate based at least in part on the determined force component.

2. The vehicle of claim 1, wherein the force component is a total force on a center of gravity of the vehicle multiplied times a sine of an angle between the direction of the force and the direction to a roll axis.

3. The vehicle of claim 1, wherein the measurement of y-axis acceleration by the accelerometer enables detection of slippage of a tire of the vehicle based on a change in lateral acceleration.

4. The vehicle of claim 1, wherein the one or more CMGs comprise two CMGs with angular momentum vectors in opposite directions such that a nominal angular momentum vector sum is zero and along the roll axis of the vehicle.

5. The vehicle of claim 1, further comprising the processor to determine a steering augmentation value to modify a steering command for the vehicle, the processor to modify the determination of the force component and CMG command based on the steering augmentation value.

6. A control system for a two-wheeled vehicle comprising:
    an inertial measurement unit (IMU);
    one or more control moment gyroscopes (CMGs);

one or more CMG controllers to control the one or more CMGs;

a processor:
to augment a steering command by a determined steering augmentation value,
and
modify a determination of a CMG command for the one or more CMG controllers based at least in part on application of the steering augmentation value.

7. The control system of claim 6, wherein application of the steering augmentation value is to cause a CMG gimbal rate to be advanced.

8. The control system of claim 7, wherein the application of the steering augmentation value is to reduce an amount of CMG compensation required for control of the vehicle.

9. The control system of claim 6, wherein the steering augmentation is to start the vehicle to roll in a correct direction, the steering augmentation being in an opposite direction as the steering command.

10. The control system of claim 6, wherein the steering augmentation is to operate as a backup CMG control upon a failure of the one or more CMGs.

11. A method comprising:
measuring with an accelerometer a y-axis acceleration for a two-wheeled vehicle, a y-axis of the vehicle being perpendicular to a direction of travel of the vehicle and parallel to a ground surface, the vehicle including one or more control moment gyroscopes (CMGs), wherein measuring with the accelerometer the y-axis acceleration for the two-wheeled vehicle comprises detecting a leakage in a value of sine of an error angle times a vector sum of a gravitational acceleration and a centrifugal acceleration of the two-wheeled vehicle;
calculating a roll angle for the vehicle based at least in part on the y-axis acceleration measured by the accelerometer;
determining a force component based at least in part on the calculated roll angle; and
generating a CMG command for a CMG gimbal rate based at least in part on the determined force component.

12. The method of claim 11, wherein the force component is a total force on a center of gravity of the vehicle multiplied times a sine of an angle between the direction of the force and the direction to a roll axis.

13. The method of claim 11, further comprising detecting slippage of a tire of the vehicle based on a change in lateral acceleration using the measurement by the accelerometer.

14. The method of claim 11, further comprising determining a steering augmentation to modify a steering command.

15. The method of claim 14, wherein the generation of the CMG command is further based at least in part on the steering augmentation.

16. The method of claim 15, wherein application of the steering augmentation is to cause a CMG gimbal rate to be advanced.

17. The method of claim 16, wherein application of the steering augmentation is to reduce an amount of CMG compensation required for control of the vehicle.

18. The method of claim 15, further comprising providing a backup CMG control utilizing the steering augmentation upon a failure of the one or more CMGs.

19. The method of claim 14, wherein the steering augmentation is to start the vehicle to roll in a correct direction, the steering augmentation being in an opposite direction as the steering command.

* * * * *